(12) United States Patent
Karunasiri

(10) Patent No.: US 9,609,444 B2
(45) Date of Patent: *Mar. 28, 2017

(54) SOUND PROCESSORS HAVING CONTAMINATION RESISTANT CONTROL PANELS AND IMPLANTABLE COCHLEAR STIMULATION SYSTEMS INCLUDING THE SAME

(71) Applicant: Advanced Bionics AG, Staefa (CH)

(72) Inventor: Rankiri Tissa Karunasiri, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/292,966

(22) Filed: Oct. 13, 2016

(65) Prior Publication Data

US 2017/0034636 A1     Feb. 2, 2017

Related U.S. Application Data

(63) Continuation of application No. 13/977,985, filed as application No. PCT/US2012/020506 on Jan. 6, 2012, now Pat. No. 9,491,530.

(60) Provisional application No. 61/431,800, filed on Jan. 11, 2011.

(51) Int. Cl.
*H04R 25/00*   (2006.01)
*H04R 1/12*    (2006.01)
*A61N 1/372*   (2006.01)
*A61N 1/375*   (2006.01)

(52) U.S. Cl.
CPC .......... *H04R 25/556* (2013.01); *A61N 1/375* (2013.01); *A61N 1/37223* (2013.01); *H04R 1/12* (2013.01); *H04R 2225/61* (2013.01); *H04R 2430/01* (2013.01)

(58) Field of Classification Search
CPC .. A61N 1/375; A61N 1/3721; A61N 1/37223; H04R 25/556; H04R 1/12; H04R 2225/61; H04R 2430/01
USPC ..... 381/23.1, 312, 330, 331; 607/55–57, 60, 607/16, 30, 32, 36, 29; 335/205–207
See application file for complete search history.

(56) References Cited

U.S. PATENT DOCUMENTS

| | | |
|---|---|---|
| 2,863,996 A | 12/1958 | Hill |
| 3,356,875 A | 12/1967 | Weismann |
| 4,315,111 A | 2/1982 | Thomas |
| 4,467,145 A | 8/1984 | Borstel |
| 4,578,628 A | 3/1986 | Siwiak |
| 4,751,485 A | 6/1988 | Fujio et al. |
| 4,782,355 A | 11/1988 | Sakai et al. |
| 4,879,443 A | 11/1989 | Carlucci et al. |
| 4,918,737 A | 4/1990 | Luethi |

(Continued)

FOREIGN PATENT DOCUMENTS

| | | |
|---|---|---|
| DE | 3723809 A1 | 1/1989 |
| DE | 10228828 C1 | 10/2003 |

(Continued)

OTHER PUBLICATIONS

PCT International Search Report and Written Opinion dated May 10, 2012 for PCT App. Ser. No. PCT/US2012/020506.

(Continued)

*Primary Examiner* — David Ton
(74) *Attorney, Agent, or Firm* — Henricks, Slavin & Holmes LLP

(57) ABSTRACT

Sound processors and systems including sound processors are disclosed.

21 Claims, 9 Drawing Sheets

(56) References Cited

U.S. PATENT DOCUMENTS

| | | |
|---|---|---|
| 5,553,152 A | 9/1996 | Newton |
| 5,659,621 A | 8/1997 | Newton |
| 5,824,022 A | 10/1998 | Zilberman et al. |
| 5,945,929 A | 8/1999 | Westra |
| 5,948,006 A | 9/1999 | Mann |
| 6,269,266 B1 | 7/2001 | Leysieffer |
| 6,272,382 B1 | 8/2001 | Faltys |
| 6,818,845 B2 | 11/2004 | Portmann |
| 6,831,988 B2 | 12/2004 | Vonlanthen |
| 7,003,876 B2 | 2/2006 | Crawford et al. |
| 7,012,200 B2 | 3/2006 | Moller |
| 7,016,511 B1 | 3/2006 | Shennib |
| 7,069,063 B2 | 6/2006 | Halkosaari et al. |
| 7,117,286 B2 | 10/2006 | Falcon |
| 7,194,101 B2 | 3/2007 | Vonlanthen |
| 7,248,712 B2 | 7/2007 | Gabathuler |
| 7,260,232 B2 | 8/2007 | Shennib |
| D560,808 S | 1/2008 | Jurkiewicz |
| 7,349,741 B2 | 3/2008 | Maltan et al. |
| 7,394,911 B2 | 7/2008 | Joergensen et al. |
| 7,440,579 B2 | 10/2008 | Vonlanthen |
| 7,450,732 B2 | 11/2008 | Kragelund |
| 7,477,753 B2 | 1/2009 | Buckley et al. |
| 7,529,587 B2 | 5/2009 | Single |
| 7,566,296 B2 | 7/2009 | Zimmerling et al. |
| 7,578,628 B2 | 8/2009 | Sherman et al. |
| 7,602,929 B2 | 10/2009 | Topholm et al. |
| 7,660,633 B2 | 2/2010 | Darley et al. |
| 7,729,774 B1 | 6/2010 | Lynch et al. |
| 7,751,898 B2 | 7/2010 | Ibrahim et al. |
| 8,352,037 B2 | 1/2013 | Darley et al. |
| 8,437,860 B1 | 5/2013 | Crawford et al. |
| 8,750,546 B2 | 6/2014 | Meier et al. |
| 9,294,852 B2 | 3/2016 | Meier et al. |
| 9,491,530 B2 | 11/2016 | Karunasiri |
| 2001/0046808 A1 | 11/2001 | Jorgensen et al. |
| 2003/0057075 A1 | 3/2003 | Portmann |
| 2004/0012470 A1 | 1/2004 | Zimmerling et al. |
| 2004/0052388 A1 | 3/2004 | Niederdrank et al. |
| 2004/0073275 A1 | 4/2004 | Malan et al. |
| 2004/0159535 A1 | 8/2004 | Wagner |
| 2004/0252855 A1 | 12/2004 | Vasserman et al. |
| 2005/0008178 A1 | 1/2005 | Joergensen |
| 2005/0033384 A1 | 2/2005 | Sacha |
| 2006/0126876 A1 | 6/2006 | Shennib |
| 2007/0127757 A2 | 6/2007 | Darbut et al. |
| 2007/0147643 A1 | 6/2007 | Grafenberg |
| 2007/0154042 A1 | 7/2007 | Buckley et al. |
| 2007/0171013 A1 | 7/2007 | Fujimori et al. |
| 2007/0253584 A1 | 11/2007 | Rass |
| 2008/0060917 A1 | 3/2008 | Chia-Li et al. |
| 2008/0232623 A1 | 9/2008 | Solum et al. |
| 2008/0288022 A1 | 11/2008 | Van der Borght et al. |
| 2009/0123013 A1 | 5/2009 | Leong |
| 2009/0239135 A1 | 9/2009 | Wang et al. |
| 2009/0325046 A1 | 12/2009 | Yang |
| 2010/0032267 A1 | 2/2010 | Gabathuler et al. |
| 2010/0260367 A1 | 10/2010 | Hasler et al. |
| 2011/0103627 A1 | 5/2011 | Meier et al. |
| 2014/0270299 A1 | 9/2014 | Meier et al. |

FOREIGN PATENT DOCUMENTS

| | | |
|---|---|---|
| EP | 0573471 B1 | 10/1994 |
| EP | 0982784 B1 | 4/2002 |
| EP | 0779015 B1 | 7/2002 |
| EP | 1271898 B1 | 1/2003 |
| EP | 1496530 B2 | 10/2006 |
| GB | 2133133 A | 7/1984 |
| JP | 05002960 A | 1/1993 |
| JP | 2003210395 A | 7/2003 |
| JP | 2009021910 A2 | 1/2009 |
| WO | WO-9216002 A1 | 9/1992 |
| WO | WO-9607295 A1 | 3/1996 |
| WO | WO-9850281 | 11/1998 |
| WO | WO-2004050166 A1 | 6/2004 |
| WO | WO-2005048474 A1 | 5/2005 |
| WO | WO-2005062668 A1 | 7/2005 |
| WO | WO-2006071210 A1 | 7/2006 |
| WO | WO-2007117721 | 10/2007 |
| WO | WO-2009118047 | 10/2009 |
| WO | WO-2009127745 | 10/2009 |
| WO | WO-2012/103320 A1 | 8/2012 |

OTHER PUBLICATIONS

Wikipedia, "Rotary Encoder", Jan. 1, 2010.
Wikipedia, "Linear Encoder", Oct. 18, 2010.

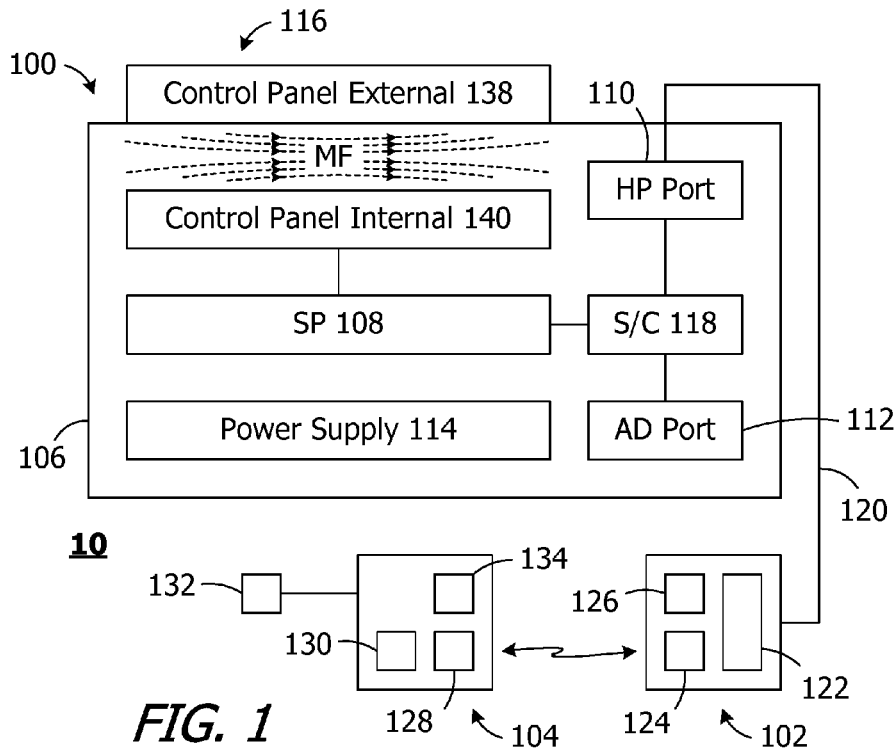
FIG. 1
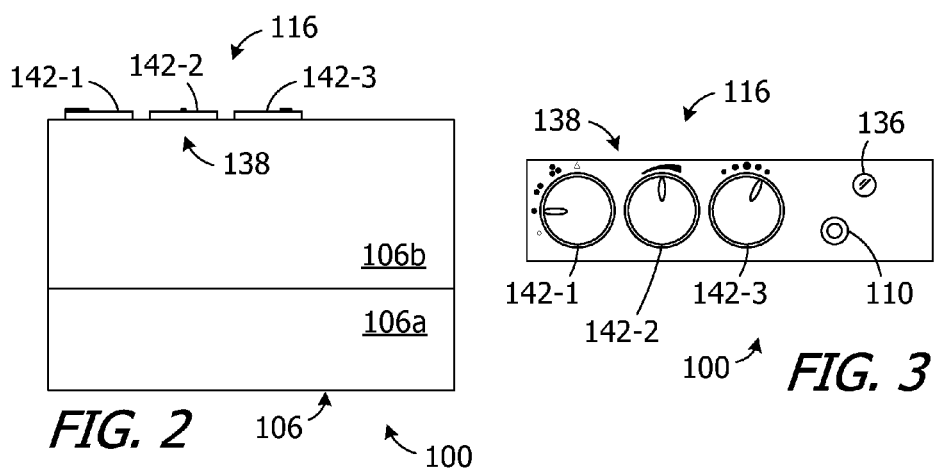
FIG. 2
FIG. 3

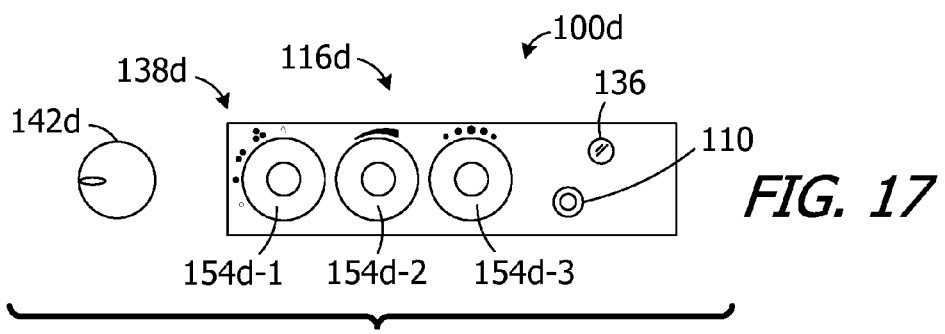
FIG. 17
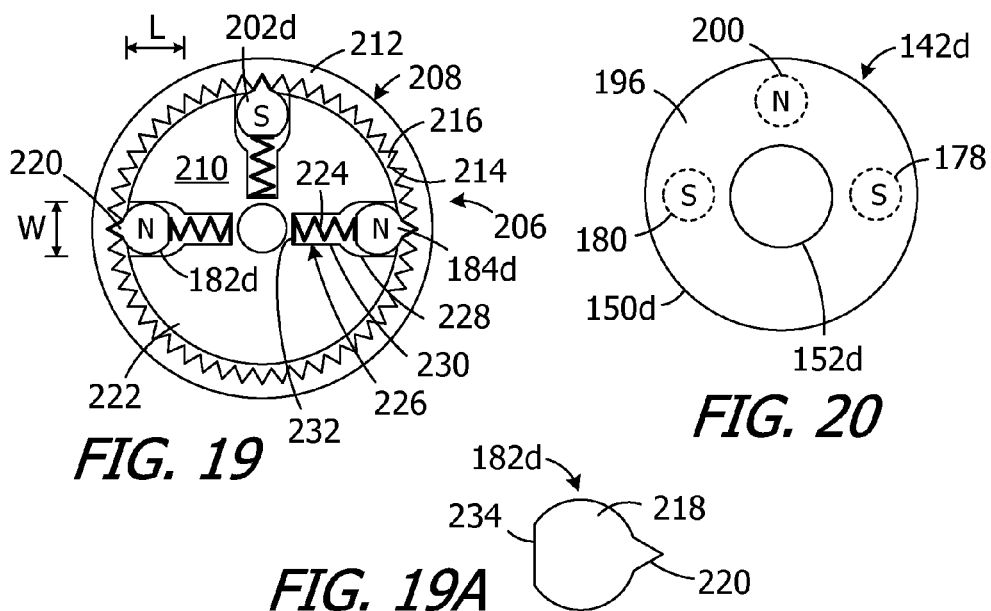
FIG. 18
FIG. 19
FIG. 19A
FIG. 20

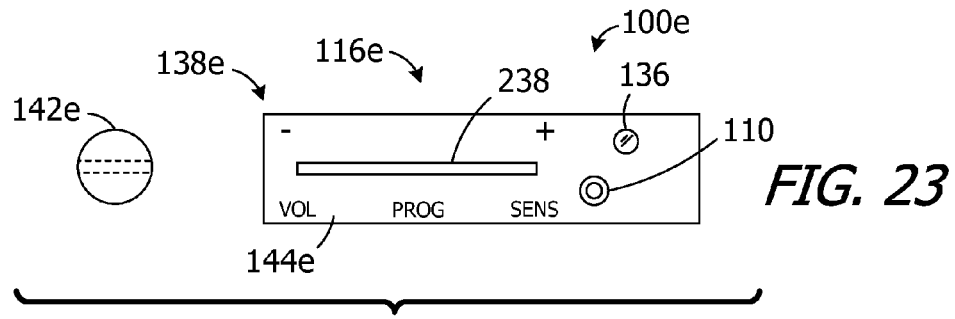
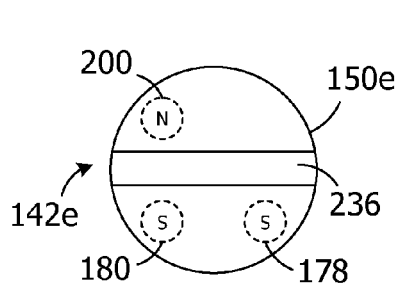
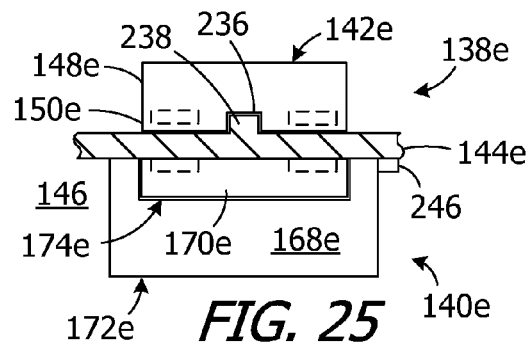
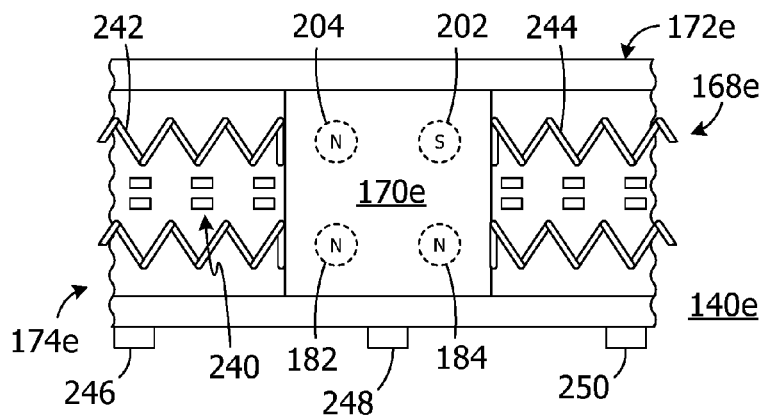
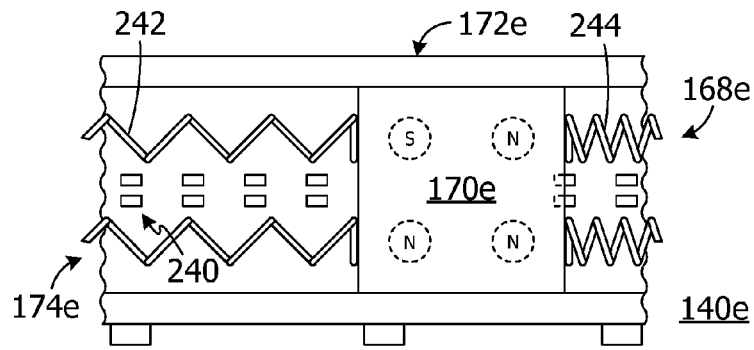

SOUND PROCESSORS HAVING CONTAMINATION RESISTANT CONTROL PANELS AND IMPLANTABLE COCHLEAR STIMULATION SYSTEMS INCLUDING THE SAME

CROSS-REFERENCE TO RELATED APPLICATIONS

This application is a continuation of U.S. application Ser. No. 13/977,985, having a 371(c) date of Jul. 23, 2013, now U.S. Pat. No. 9,491,530, which is the U.S. National Stage of PCT App. Ser. No. PCT/US2012/020506, filed Jan. 6, 2012, which claims priority to U.S. Prov. App. Ser. No. 61/431,800, filed Jan. 11, 2011.

BACKGROUND

1. Field

The present disclosure relates generally to sound processors such as, for example, the sound processors in implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Sound processor With Remote Control" and incorporated herein by reference in its entirety.

As alluded to above, some ICS systems include an implantable device, a sound processor with sound processing circuitry, and a microphone that is in communication with the sound processor. The implantable device communicates with the sound processor and, to that end, some ICS systems include a headpiece that is in communication with both the sound processor and the implantable device. In one type of ICS system, the sound processor is worn behind the ear (or "BTE") sound processor, while other types of ICS systems have a body worn sound processor. The body worn sound processor, which is larger and heavier than a BTE sound processor, is typically worn on the user's belt or carried in the user's pocket. One example of a conventional body worn sound processor is the Advanced Bionics Platinum Series body worn sound processor.

Sound processors include various control structures that may be employed by the user to control certain operational parameters (e.g. a volume knob, a sensitivity knob and/or a program selector knob). The control structures are mechanically connected, by way of openings in the sound processor housing, to structures within the housing so that movement of the control structure (e.g. rotation of a knob) can be detected and the associated operational parameter adjusted accordingly. The openings in the sound processor housing for the mechanical connections necessitate the use of seals to prevent the ingress of liquid, dust, and other contaminants. The present inventor has determined that, despite the use of seals, such control structures can be the source of leaks and other kinds of contamination.

SUMMARY

A sound processor in accordance with at least one of the present inventions includes a housing, sound processor circuitry, an external movable element and an internal control device with a control device movable member. The external movable element is magnetically coupled to the internal control device movable member such that movement of the external movable member results in corresponding movement of the control device movable member. The present inventions also include cochlear stimulation systems with such a sound processor.

A sound processor in accordance with at least one of the present inventions includes a housing, sound processor circuitry, and a control panel, associated with the housing, including an external portion, a control panel wall, and an internal portion that is operably connected to the sound processor circuitry and magnetically coupled to the external portion such that movement of the external portion is transferred to the internal portion. The present inventions also include cochlear stimulation systems with such a sound processor.

A method in accordance with at least one of the present inventions includes the step of controlling an operational parameter of a sound processor by imparting movement to a portion of an internal encoder or potentiometer with an external device that is magnetically coupled to the internal encoder or potentiometer.

Such sound processors, systems and methods are advantageous for a variety of reasons. For example, the present inventors have determined that by imparting movement (e.g., rotational movement associated with user volume control) to an internal control device by way of magnetic force instead of a direct mechanical connection, the aforementioned openings that extend all the way through the housing may be omitted, as may the aforementioned seals, and a potential source of sound processor contamination eliminated.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a functional block diagram of an ICS system in accordance with one embodiment of a present invention.

FIG. 2 is a front view of a sound processor in accordance with one embodiment of a present invention.

FIG. 3 is a top view of a sound processor in accordance with one embodiment of a present invention.

FIG. 17 is a top view of a sound processor in accordance with one embodiment of a present invention with the rotatable element detached.

FIG. 18 is a partial section view of a portion of a control panel in accordance with one embodiment of a present invention with the rotatable element detached.

FIG. 19 is a plan view of a portion of the control panel illustrated in FIG. 17 in a locked state.

FIG. 19A is a plan view of a portion of the control panel illustrated in FIG. 18.

FIG. 20 is a plan view of a portion of the control panel illustrated in FIG. 18.

FIG. 23 is a top view of a sound processor, with a control panel, in accordance with one embodiment of a present invention with the rotatable element detached.

FIG. 24 is a plan view of a portion of the control panel illustrated in FIG. 23.

FIG. 25 is a partial section view of the control panel illustrated in FIG. 23.

FIG. 26 is a plan view of a portion of the control panel illustrated in FIG. 23.

FIG. 27 is a plan view of a portion of the control panel illustrated in FIG. 23.

DETAILED DESCRIPTION OF THE EXEMPLARY EMBODIMENTS

Figure 4:
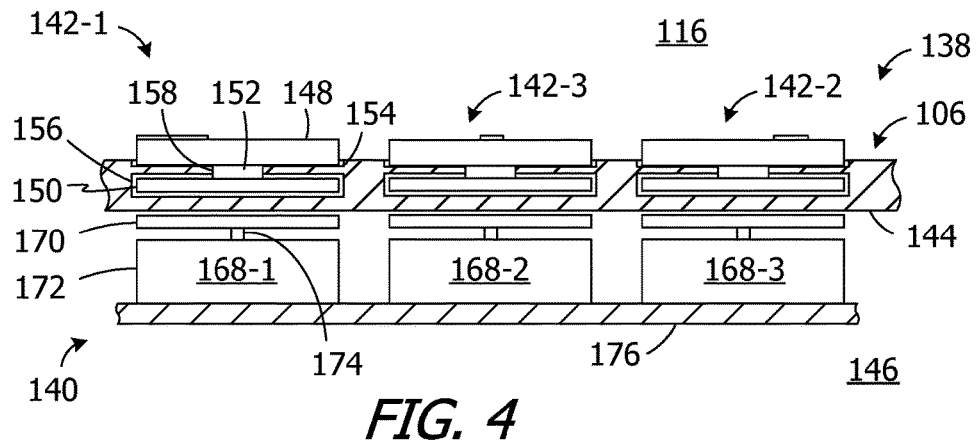
FIG. 4 is a partial section view of a control panel in accordance with one embodiment of a present invention.

The following is a detailed description of the best presently known modes of carrying out the inventions. This description is not to be taken in a limiting sense, but is made merely for the purpose of illustrating the general principles of the inventions.

The present inventions have application in a wide variety of systems that provide sound (i.e. either sound or a perception of sound) to the hearing impaired as well as others who require such systems on a situational basis. One example of such a system is an ICS system where an external body worn sound processor communicates with a cochlear implant and, accordingly, the present inventions are discussed in the context of such ICS systems. The present inventions are not, however, limited to ICS systems and may be used in combination with other systems for the hearing impaired that currently exist, or are yet to be developed. Nor are the present inventions limited to ICS systems with body worn sound processors. The present inventions are also applicable to, for example, ICS systems with BTE sound processors.

One example of a sound processor is the body worn sound processor generally represented by reference numeral 100 in FIGS. 1-3. The exemplary sound processor 100, which may be combined with a headpiece 102 and a cochlear implant 104 to form an ICS system 10, includes a housing 106 in which and/or on which various components are supported. Such components may include, but are not limited to, sound processor circuitry 108 (e.g., a microprocessor and memory) that converts sound to pulse sequences and performs the other control functions, a headpiece port 110, an auxiliary device port 112 for an auxiliary device such as a mobile phone or a music player, a permanent or removable power supply 114 (e.g. rechargeable and disposable batteries or other electrochemical cells), and a control panel 116. The headpiece port 110 and auxiliary device port 112 may be connected to the sound processor circuitry 108 by way of, for example, a signal splitter/combiner 118 such as that found in the Platinum Signal Processor body worn unit from Advanced Bionics Corporation. In those instances where the power supply 114 is removable (e.g. for replacement or recharging) the housing 106 may be provided with a power supply portion 106a for the power supply and a main portion 106b for the remainder of the sound processor. The power supply portion 106a may be a "battery pack" in which the power supply 114 is permanently housed, or may simply be a cover that may be removed from the main portion 106b to obtain access to the power supply 114.

The headpiece 102 in the exemplary ICS system 10 (FIG. 1) includes a cable 120 which may be connected to the headpiece port 110, a microphone 122, a transmitter 124 (e.g. an antenna) and a positioning magnet 126. The exemplary cochlear implant 104 includes a receiver 128 (e.g. an antenna), an internal processor 130, a cochlear lead 132 with an electrode array, and a positioning magnet (or magnetic material) 134. The transmitter 124 and receiver 128 communicate by way of electromagnetic induction, radio frequencies, or any other wireless communication technology. The positioning magnet 126 and positioning magnet (or magnetic material) 134 position the headpiece antenna 124 over the cochlear implant antenna 128. During use, the microphone 122 picks up sound from the environment and converts it into electrical impulses, and the sound processor 100 filters and manipulates the electrical impulses and sends the processed electrical signals through the cable 120 to the transmitter 124. Electrical impulses received from an auxiliary device are processed in essentially the same way. The receiver 128 receives signals from the transmitter 124 and sends the signals to the cochlear implant internal processor 130, which modifies the signals and passes them through the cochlear lead 132 to the electrode array. The electrode array may be wound through the cochlea and provides direct electrical stimulation to the auditory nerves inside the cochlea. This provides the user with sensory input that is a representation of external sound waves which were sensed by the microphone 122.

It should be noted that, in other implementations, communication between the sound processor and a headpiece and/or auxiliary device may be accomplished through wireless communication techniques. It should also be noted that, in other implementations, the sound processor may be configured to directly communicate with the cochlear implant (i.e. without a headpiece and associated cable).

A visible indicator 136, such as a multicolor LED, may be provided near the control panel 116. The visible indicator 136 may be used to provide information about the sound processor 100. Such information may include, but is not limited to, battery charge status, lock status, and microphone/system status.

The exemplary sound processor 100 may be carried by the user in a variety of ways. By way of example, but not limitation, the sound processor 100 may be carried in the user's pocket, secured to a belt with a belt clip that is either part of housing 106 or a separate carrier, or placed in a harness that is configured to be worn by a small child.

The exemplary control panel 116 has a control panel external portion 138 that is associated with the exterior of the housing 106 and a control panel internal portion 140 that is located within the housing. As discussed in greater detail below, movement associated with user manipulation of the control panel external portion 138 (e.g., rotational or linear movement) is transferred to the internal portion 140 by way of magnetic force MF instead of a direct mechanical connection (e.g. a post that extends completely through the housing). As such, the aforementioned openings that extend all the way through the housing wall (i.e. from the exterior to the interior) may be omitted, as may the aforementioned seals, and a potential source of sound processor contamination is eliminated.

In the illustrated embodiment illustrated in FIGS. 1-3, and although the number may be increased or decreased to suit the intended application, the control panel external portion 138 includes three rotatable elements 142-1, 142-2 and 142-3. For example, the rotatable element 142-1 may be used to select the appropriate sound processing program as well as to turn the sound processor 100 on and off, the rotatable element 142-2 may be used to control volume, and the rotatable element 142-3 may be used to control sensitivity.

Figure 5:
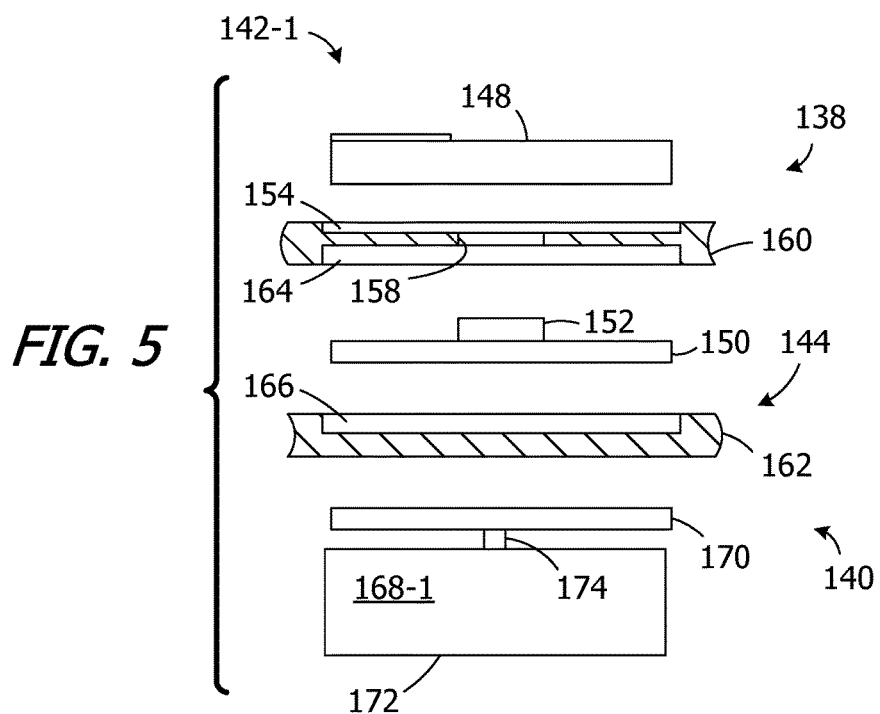
FIG. 5 is an exploded partial section view of a portion of the control panel illustrated in FIG. 4.
Figure 6:
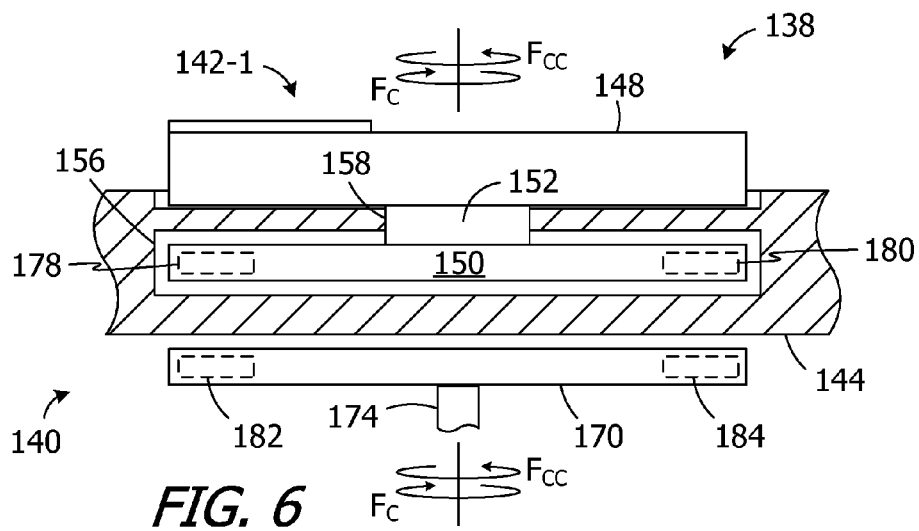
FIG. 6 is a partial section view of a portion of the control panel illustrated in FIG. 4.
Figure 7:
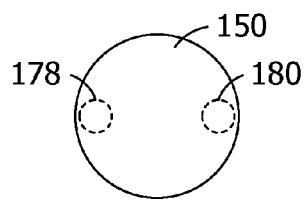
FIG. 7 is a plan view of a portion of the control panel illustrated in FIG. 4.
Figure 8:
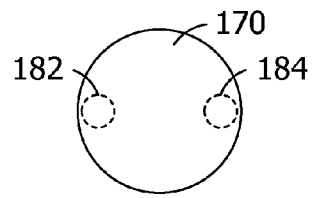
FIG. 8 is a plan view of a portion of the control panel illustrated in FIG. 4.
Figure 9:
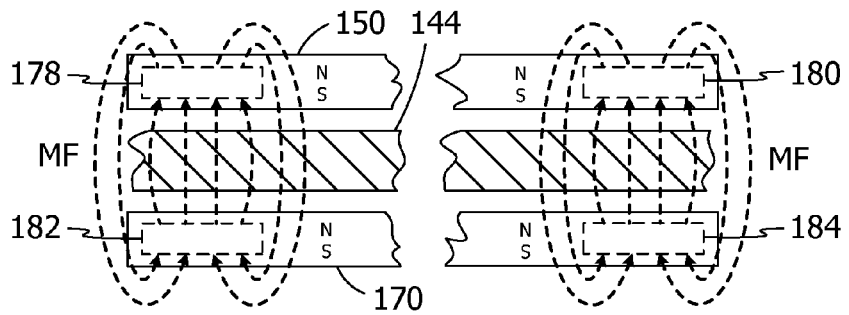
FIG. 9 is a partial section view of showing the magnetic attraction between external and internal portions of the control panel illustrated in FIG. 4.

Turning to FIGS. 4 and 5, the housing 106 includes a control panel wall 144 that separates the control panel external portion 138 from both the control panel internal portion 140 and the housing interior 146. The rotatable elements 142-1, 142-2 and 142-3, which are identical in the illustrated embodiment, each includes a rotatable knob 148, a magnet carrier 150 (with one or more magnets as discussed below) and an axle 152 that connects the knob to the magnet carrier. Although the present inventions are not limited to any particular shapes, the exemplary knob 148 and a magnet carrier 150 are disk-shaped and the axle 152 is cylindrical. The control panel wall 144 may be configured to rotatably mount the rotatable elements 142-1, 142-2 and 142-3 to the housing 106. For example, the control panel wall 144 may include a recess 154 for the knob 148, a cavity 156 for the magnet carrier 150, and an aperture 158 for the axle 152. The recesses 154 may be formed in a variety of ways. For example, the control panel wall 144 may be formed from two wall portions 160 and 162 (FIG. 5), each of which includes respective pluralities of disk-shaped cavity portions 164 and 166. The wall portions 160 and 162 are joined to one another during assembly, thereby forming the cavities 156 and entrapping the magnet carriers 150.

It should be noted that the exemplary cavity 156 and aperture 158 do not, individually or collectively, extend all the way through the control panel wall 144 to the housing interior 146. The cavity 156 and aperture 158 merely extend into the control panel wall 144 and, accordingly, contaminants that enter the cavity and aperture will not enter the housing interior 146.

The internal portion 140 of the exemplary control panel 116 includes rotation responsive control devices 168-1, 168-2 and 168-3 (FIG. 4) that are respectively magnetically coupled to, and have portions that rotate with, the rotatable elements 142-1, 142-2 and 142-3. The rotation responsive control devices 168-1, 168-2 and 168-3 are also operably connected to the sound processor circuitry 108 (or other control circuitry) and produce a control output in response to the rotation of a portion thereof. Suitable examples of rotation responsive control devices include, but are not limited to, encoders and potentiometers. The control output associated with an encoder may be an analog or digital signal, while the control output associated with a potentiometer may be a variable resistance.

The exemplary rotation responsive control devices 168-1, 168-2 and 168-3, which are identical in the illustrated embodiment, may include a rotatable portion 170, a fixed portion 172 and an axle 174 that rotatably mounts the rotatable portion to the fixed portion. The rotatable portion 170 is magnetically coupled to the magnet carrier 150 of the associated rotatable element (e.g., rotatable element 142-1) such that rotation of the magnet carrier is transferred to the rotatable portion, i.e. the rotatable portion 170 rotates with the magnet carrier 150. To that end, and as discussed in greater detail below, the rotatable portion 170 carries magnets or other elements formed from magnetic material. The rotation responsive control devices 168-1, 168-2 and 168-3 may be mounted within housing interior 146 on a circuit board 176 or other suitable instrumentality.

The manner in which movement of the rotatable portions of the rotation responsive control devices 168-1, 168-2 and 168-3 results in control output will, of course, depend on the type of control device employed. In the exemplary context of a rotational encoder, the rotatable portion 170 or the axle 174 may be provided with an optical pattern that cooperates with a light source and sensor arrangement in conventional fashion.

As shown in FIG. 4, the control panel wall 144 does not include apertures that extend all the way through the wall (i.e. from the exterior of the housing to the interior 146). Such apertures are unnecessary because the rotational movement imparted to the knobs 148 by the user is transferred to the rotation responsive control devices 168-1, 168-2 and 168-3 by way of the magnetic coupling instead of a direct mechanical connection that would require, for example, a post or other structural element which extends through the wall to connect the knobs to the control devices.

A wide variety of magnetic coupling arrangements may be used to magnetically couple the rotatable elements to the rotation responsive control devices. One exemplary magnetic coupling arrangement is illustrated in FIGS. 6-9. Here, the magnet carrier 150 includes a pair of magnets 178 and 180 and the rotatable portion 170 includes a pair of magnets 182 and 184. The north-south (N-S) orientation of the magnets is shown with N's and S's. The magnetic force MF between magnets 178 and 182 and magnets 180 and 184 is strong enough to cause the rotatable portions 170 of the rotation responsive control devices 168-1, 168-2 and 168-3 to maintain their rotational alignment with the corresponding magnet carriers 150 of the rotatable elements 142-1, 142-2 and 142-3 such that movement of the rotatable portions corresponds to that of the rotatable elements. Put another way, the rotatable portions 170 rotate with the corresponding magnet carriers 150. Put still another way, the rotational force (and movement) applied by the user to the rotatable knobs 148 is transferred to the rotatable portions 170. It should also be noted that the transfer of rotational force is bi-directional. When the user applies clockwise rotational force $F_C$ (FIG. 6) to a knob 148 that is sufficient to the cause rotation in the clockwise direction, the clockwise rotational force $F_C$ is transferred to the corresponding rotatable portion 170 by way of the magnetic force MF, and when the user applies sufficient counterclockwise rotational force $F_{CC}$ to a knob to cause rotation in the counterclockwise direction, the counterclockwise rotational force $F_{CC}$ is also transferred to the corresponding rotatable portion 170 by way of the magnetic force MF.

The rotatable elements 142-1, 142-2 and 142-3 may be identical to one another in some implementations and may be different than one another in other implementations. Similarly, the rotation responsive control devices 168-1, 168-2 and 168-3 may be identical to one another in some implementations and may be different than one another in other implementations. Suitable materials for the non-magnetic portions of the rotatable elements 142-1, 142-2 and 142-3 and the rotatable portions 170 include, but are not limited to, stainless steel, polycarbonate, and fluoropolymers such as polytetrafluoroethylene.

Figure 10:
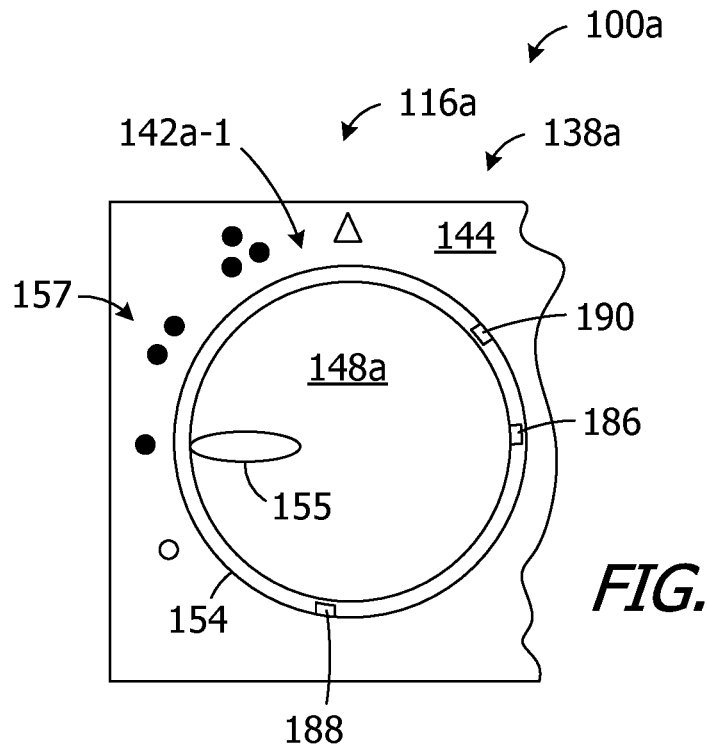
FIG. 10 is a top view of a portion of a sound processor in accordance with one embodiment of a present invention.
Figure 11:
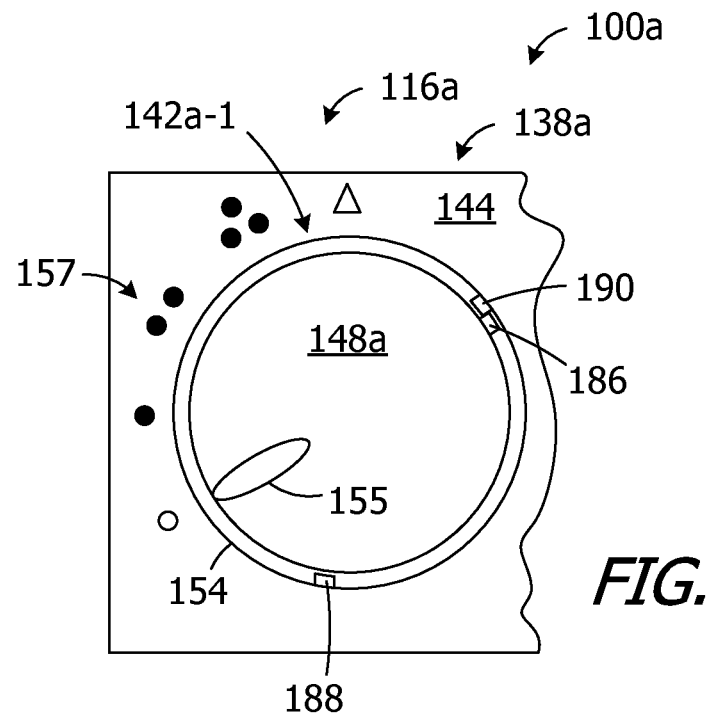
FIG. 11 is another top view of the sound processor illustrated in FIG. 10.
Figure 12:
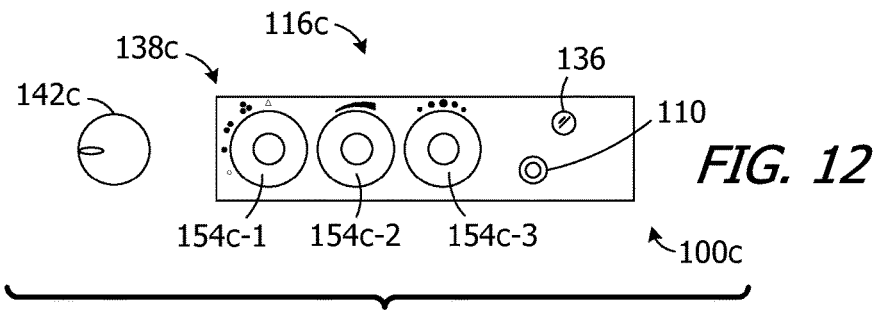
FIG. 12 is a top view of a sound processor in accordance with one embodiment of a present invention with the rotatable element detached.
Figure 13:
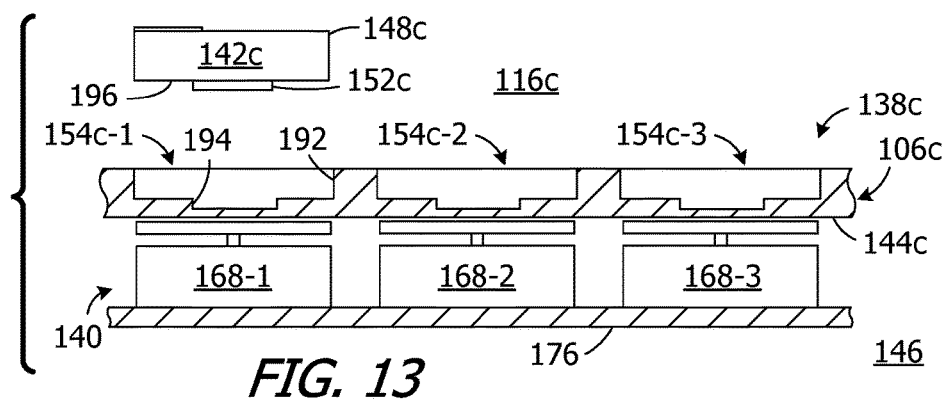
FIG. 13 is a partial section view of a control panel in accordance with one embodiment of a present invention with the rotatable element detached.
Figure 14:
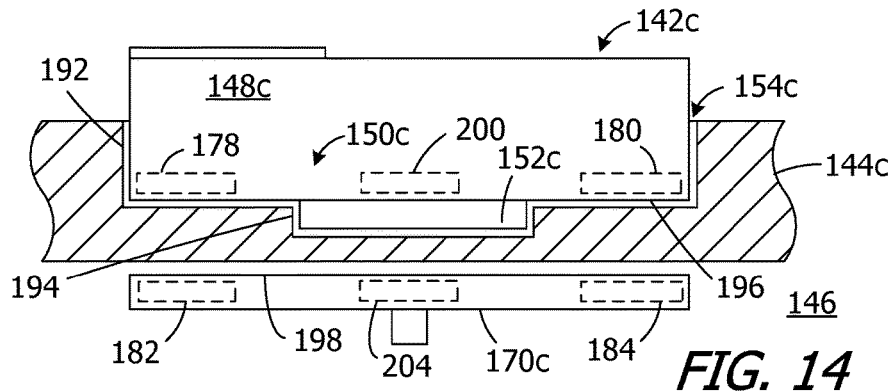
FIG. 14 is a partial section view of a portion of the control panel illustrated in FIG. 13 with the rotatable element in place.

One or more of the rotatable elements 142-1, 142-2 and 142-3 may be configured so as to limit rotation thereof to a predefined range. This may be accomplished in a variety of ways. By way of example, but not limitation, the exemplary sound processor 100a illustrated in FIGS. 10 and 11 is substantially identical to sound processor 100 and similar elements are represented by similar reference numerals. Here, however, one or more of the rotatable elements (e.g., rotatable element 142a-1) on the external portion 138a of the control panel 116a includes a knob 148a with a tab 186. A pair of stops 188 and 190 are positioned in the recess 154. The knob 148a is free to rotate the clockwise and counterclockwise directions while the tab 186 between the stops 188 and 190 (FIG. 10), but is prevented from rotating beyond the points at which the tab contacts one of the stops (FIG. 11). As a result, rotation of the knob 148a (as well as the magnet carrier 150 and rotatable portion 170) will be limited to movement between a first position where the knob indicator 155 is aligned with the "o" end of the indicia 157 and a second position where the knob indicator 155 is aligned with the "Δ" end of the indicia. Frictional engagements (not shown) that correspond to each indicia element may also be provided to generate tactile feedback as to the alignment of the knob (e.g., knob 148a) with the indicia elements.

The rotatable elements 142-1, 142-1a, 142-2 and 142-3 in the exemplary control panels 116 and 116a illustrated FIGS. 1-11 are permanently secured to underlying sound processor housing 106, i.e. the rotatable elements may not be removed from the housing without disassembly or destruction of some portion of the housing or the rotatable elements. The rotatable elements may, however, be removable in other implementations.

The exemplary sound processor 100c illustrated in FIGS. 12-16 is substantially identical to sound processor 100 and similar elements are represented by similar reference numerals. For example, the sound processor 100c has a control panel 116c with a wall 144c that does not include apertures which extend all the way through the wall. Here, however, the external portion 138c of the control panel 116c includes a single removable rotatable element 142c and three recesses 154c-1, 154c-2 and 154c-3 that are configured to receive the rotatable element. The rotatable element 142c includes a knob 148c and an axle 152c. The recesses 154c-1, 154c-2 and 154c-3, which are respectively aligned with the rotation responsive control devices 168-1, 168-2 and 168-3, each includes a knob receiving portion 192 and an axle receiving portion 194 to accommodate the knob 148c and axle 152c. The removable rotatable element 142c also includes a magnet carrier 150c that may be integral with the knob 148c (as shown), or may be a separate structural element.

The rotatable element magnet carrier 150c and the rotatable portions 170c of each control device 168-1, 168-2 and 168-3 in the exemplary control panel 116c may be provided with magnets. When the rotatable element 142c is positioned in one of the recesses 154c-1, 154c-2 and 154c-3, the magnetic force between the magnets will be strong enough to cause the rotatable portion 170c of the corresponding (i.e. axially aligned) one of the control device 168-1, 168-2 and 168-3 to maintain its rotational alignment with the magnet carrier 150c, as is described in above, such that the rotatable portion will rotate with the magnet carrier.

Any suitable magnetic coupling arrangement may be employed in the exemplary control panel 116c. For example, the magnetic coupling arrangement illustrated in FIGS. 6-9 may be employed. The magnetic coupling arrangement illustrated in FIGS. 6-9 is configured so as to insure that the rotational orientation of the rotatable element 142c and each rotatable portion 170c will remain constant. In other words, after being removed from one of the recesses 154c-1, 154c-2 and 154c-3 in the wall 144c of housing 106c, the rotatable element 142c will return to prior rotational orientation when it is returned to that recess.

Figure 15:
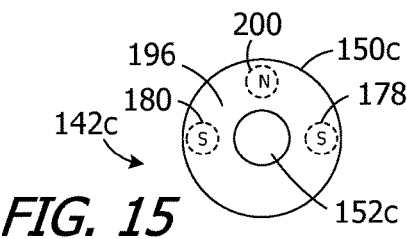
FIG. 15 is a plan view of a portion of the control panel illustrated in FIG. 12.
Figure 16:
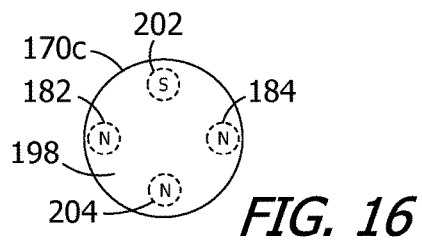
FIG. 16 is a plan view of a portion of the control panel illustrated in FIG. 12.

Referring more specifically to FIGS. 15 and 16, the magnet carrier 150c of rotatable element 142c includes magnets 178 and 180 and the control device rotatable portions 170c each includes magnets 182 and 184. The magnets 178-184 are oriented in the same manner that they are in the embodiment illustrated in FIGS. 6-9. Specifically, the magnets 178 and 180 on the magnet carrier 150c are oriented such that the south (S) poles are adjacent the bottom surface 196 (i.e., the south poles face the wall 144c) and the magnets 182 and 184 on the rotatable portions 170c are oriented such that the north (N) poles are adjacent the top surface 198 (i.e., the north poles face the wall 144c). The magnet carrier 150c and control device rotatable portions 170c may also be provided with magnets that, in addition to augmenting the magnetic coupling, insure proper orientation by creating a repulsion force when the rotatable element 142c is placed in one of the recesses 154c-1, 154c-2 and 154c-3 in an improper orientation. For example, the magnet carrier 150c has a magnet 200 that is oriented such that the north (N) pole is adjacent the bottom surface 196 (i.e., the north pole faces the wall 144c) and the rotatable portions 170c include magnets 202 and 204 are oriented such that the south pole (S) of magnet 202 is adjacent the top surface 198 (i.e., the south pole faces the wall 144c) and the north (N) pole of magnet 204 is adjacent the top surface 198 (i.e., the north pole faces the wall 144c).

Proper orientation of the rotatable element 142c relative to the associated rotation responsive control device (e.g., control device 168-1 when the rotatable element is positioned in recess 154c-1) in the following N-S magnet alignments: magnets 178/182, 180/184 and 200/202. If the rotatable element 142c is offset from the proper orientation, there will be N-N and/or S-S magnet alignments that create a repulsion force which prevents the rotatable element 142c from being properly seated in the recess. For example, 90 degree misalignment would result in a S-S magnet alignment (i.e., magnets 178/202) and a N-N magnet alignment (i.e., magnets 200/184), and a 180 degree misalignment would result in a N-N magnet alignment (i.e., magnets 200/204). In any case of misalignment, the user need only rotate the rotatable element 142c until there is proper rotational orientation, at which time the rotatable element will be drawn to the recess that the magnetic attraction force (and lack of repulsion force) associated with the 178/182, 180/184 and 200/202 magnet alignments.

In other implementations, inadvertent or unauthorized operation of the control panel may be prevented by way of a locking mechanism that prevents rotation of the rotatable portion of the rotation responsive control devices unless the intended rotatable element is present. One example of a sound processor that includes such a locking mechanism is generally represented by reference numeral 100d in FIG. 17. The exemplary sound processor 100d is substantially identical to sound processor 100c and similar elements are represented by similar reference numerals. For example, the sound processor 100d has a control panel 116d with a wall 144d without apertures, a plurality of recesses 154d-1, 154d-2 and 154d-3 that are configured to receive a rotatable element 142d with a knob 148d and axle 152d, and a corresponding plurality of rotation responsive control devices.

Figure 21:
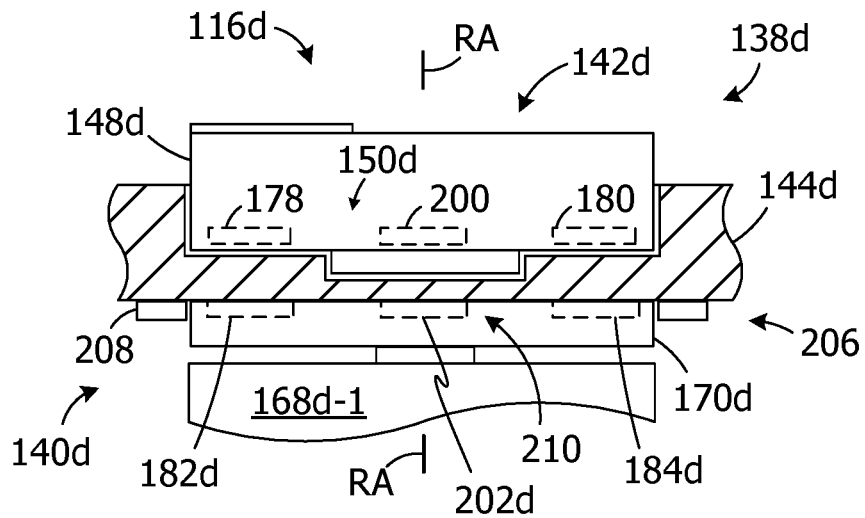
FIG. 21 is a partial section view of a portion of the control panel illustrated in FIG. 18 with the rotatable element in place.
Figure 22:
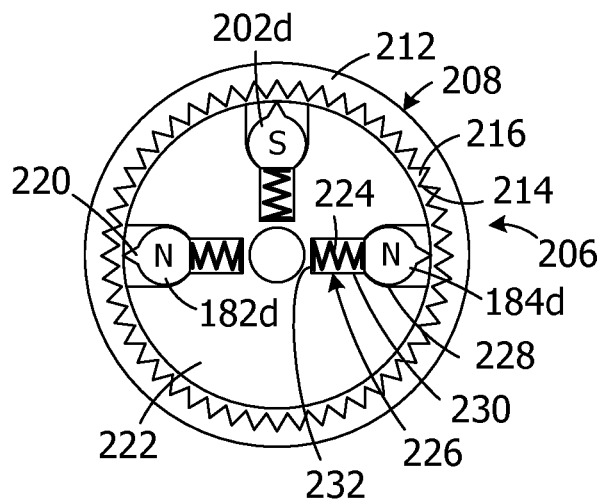
FIG. 22 is a plan view of a portion of the control panel illustrated in FIG. 18 in an unlocked state.

Referring to FIGS. 18-22, in the exemplary control panel 116d, a lock 206 may be associated with one, some, or all of the rotation responsive control devices (e.g., control device 168d-1). The lock 206 prevents the associated rotatable portion 170d from rotating when in the locked state (FIGS. 18-19) and allows the rotatable portion to rotate when in the unlocked state (FIGS. 21-22). The exemplary lock 206 includes a fixed element 208 that is carried by the wall 144d (or other structure) and a movable element 210, which is carried by the rotatable portion 170d, that engages the fixed element when the lock is in the locked state.

Referring to FIG. 19, the exemplary fixed element 208 includes an annular frame 212 and a plurality of inwardly facing projections 214 that define gaps 216 therebetween. The exemplary movable element 210 includes, among other things, magnets 182d, 184d and 202d. The magnets 182d, 184d and 202d magnetically couple the rotatable portion 170d to the rotatable element 142d in the manner discussed above with reference to, for example, FIGS. 9 and 14-16. The magnets 182d, 184d and 202d are also the portions of the movable element 210 that engage the fixed element 208. As such, each magnet includes a main portion 218 and a protrusion 220 (FIGS. 19 and 19A) that is sized and shaped to fit into the gaps 216. With respect to the manner in which the magnets are held and moved, the movable element 210 is also provided with a magnet carrier 222 that may be integrally formed with, or mounted on, the control device rotatable portion 170d, and a plurality of springs 224 (or other biasing devices) that bias magnets toward the fixed element 208. The magnet carrier 222 has a plurality of magnet channels 226 for the magnets 182d, 184d and 202d and springs 224. Each channel 226 has a relatively wide magnet portion 228, a relatively narrow spring portion 230, and a closed end 232. The length L of the magnet portions 228 is such that the magnets can move in the radial direction from the lock position (FIG. 19) to the unlock position (FIG. 22). The width W of the magnet portions 228 is only slightly larger than the width of the associated magnet in order allow the magnet to move back and forth during locking and unlocking, while preventing relative movement between the carrier 222 and the magnets in the direction of rotation. The wall 144d defines a cover for the movable element 210 in the exemplary embodiment, although a separate cover may be provided in other implementations.

Each spring 224 in the illustrated embodiment is compressed between the closed end 232 and a flat surface 234 (FIG. 19A) on the associated magnet. As a result, and as illustrated in FIG. 19, the springs 224 bias the magnets 182d, 184d and 202d outwardly so that the movable element protrusions 220 are pressed into the fixed element gaps 216, thereby preventing rotation of the movable element 210 and the associated rotatable portion 170d. In other words, the control device 168d-1 is locked and cannot be used to adjust the operational parameter associated with control device 168d-1.

The rotatable element 142d in the illustrated implementation is configured to function as a "key" to unlock the lock 206 in addition to facilitating rotation of the rotatable portion 170d in the manner described above. To that end, the rotatable element 142d includes a magnet carrier 150d with magnets 178, 180 and 200. The rotatable element magnets 178, 180 and 200 are positioned in such a manner that, when the rotatable element 142d is placed into one of the recesses 154c-1, 154c-2 and 154c-3 and properly oriented relative to the movable element 210 (i.e., magnets 178, 180 and 200 are respectively rotationally aligned with magnets 182d, 184d and 202d) as shown in FIG. 21, the magnets 182d, 184d and 202d will be driven by magnetic force sufficient to overcome the biasing force of the springs 224 from the locked positions (FIG. 19) to the unlocked positions (FIG. 22). In particular, and referring to FIGS. 18-20, the magnets 178, 180 and 200 are located radially inward of, i.e., are closer to the rotational axis RA than, the magnets 182d, 184d and 202d. The positions of the magnets 178, 180 and 200 are also fixed within the magnet carrier 150d. As such, the magnetic forces attracting the magnets to one another will pull the magnets 182d, 184d and 202d toward (in the radial direction) the magnets 178, 180 and 200, respectively. The movable element protrusions 220 will then be free of the fixed element gaps 216 (FIGS. 21 and 22), and subsequent rotation of the rotatable element 142d will produce corresponding rotation of the control device rotatable portion 170d. Once the rotatable element 142d (and control device rotatable portion 170d) have been rotated to the desired position to accomplish, for example, a change in volume, the rotatable element may be removed. The magnets 182d, 184d and 202d will then return to the locked positions.

It should also be noted that the location and N-S orientation of the magnets 182d, 184d and 202d prevents unintended unlocking by, for example, a device (e.g., a single relatively large magnet) that does have magnets with corresponding locations and orientations.

The present inventions are not limited to locks with structures that move radially in the manner illustrated in FIGS. 19 and 22. By way of example, but not limitation, a lock with magnets that move axially (i.e. vertically in the orientation illustrated in FIGS. 18 and 21) between locking and unlocking positions may be provided.

The present inventions also are not limited to sound processors that rely on rotational movement by the user, and are also applicable to linear movement. One example of a sound processor that includes a control panel which responds to linear movement is generally represented by reference numeral 100e in FIG. 23. The exemplary sound processor 100e is substantially identical to sound processor 100c and similar elements are represented by similar reference numerals. For example, the sound processor 100e includes a control panel 116e with an internal portion 138e that is separated from an internal portion 140e by a wall 144e. The control panel wall 144e does not include an opening that extends completely therethrough. The external portion 138e also has a removable movable element 142e. Here, however, movable element 142e moves linearly.

As illustrated for example in FIGS. 23-25, the movable element 142e and wall 144e in the control external portion 138e may be respectively provided with a recess 236 and protrusion 238 that together guide movement of the movable element. The locations of the recess 236 and protrusion 238 may be reversed, or the recess and protrusion may be omitted, in other implementations. The movable element 142e also includes a knob 148e and a magnet carrier 150e with magnets 178, 180 and 200 (discussed below).

The internal portion 140e of the exemplary control panel 116e includes linear movement responsive control device 168e (FIG. 25) that has a portion which is magnetically coupled to, and moves with, the movable element 142e. The control device 168e is operably connected to the sound processor circuitry 108 (or other control circuitry) and produces a control output in response to the movement of a portion thereof. Suitable examples of such control devices include, but are not limited to, linear encoders, linear potentiometers and a series of linearly spaced switches. The illustrated example includes a linear encoder.

In the illustrated implementation, the linear movement responsive control device 168e includes a movable member 170e as well as a fixed portion 172e with a channel 174e for the movable member. The movable member 170e carries magnets 182, 184, 202 and 204 which cooperate with the magnets 178, 180 and 200 on the movable member in the manner described above. A plurality of light source and sensor arrangements 240 are arranged along the channel 174e to detect movement of the movable member 170e. The movable member 170e in the illustrated implementation also has an initial position (FIG. 26). One or more springs (or other biasing elements) 242 and 244, which are located on opposite sides of the movable member 170e, maintain the movable member at the initial position and return the movable member to the initial position after movement in the manner described below.

The exemplary control panel 116e is also provided with structure that allows the user to indicate which of the operational parameters (e.g. volume, program or sensitivity) is to be controlled in a particular control operation. In the illustrated embodiment, the internal portion 140e of control panel 116e has a plurality of sensors 246, 248 and 250 (FIGS. 25 and 26) that respectively correspond to volume, program and sensitivity. The sensors 246, 248 and 250, which are operably connected to the sound processor circuitry 108, are positioned below corresponding indicia (FIG. 23) on the outer surface of the wall 144e. The sensors may, for example, be magnetic sensors (e.g., magnetoresistive sensors, Hall effect sensors, and reed switches). Here, the user will position the movable element 142e onto the wall 144e such that one of the magnets (e.g., magnet 200) is positioned over one of the sensors 246, 248 and 250. The sound processor circuitry 108 circuitry will enter the corresponding mode, i.e., volume control, program control or sensitivity control, after the sensing and will remain in this mode for a predetermined control period (e.g. 10 seconds). Movement of the movable member 170e along the protrusion 238 during the control period will result in adjustment of the selected control parameter. In particular, movement in the direction of the "+" will result in an increase in the parameter (e.g. an increase in volume, or switching from "program 1" to "program 2"), while movement in the direction of the "−" will result in an decrease in the parameter.

Movement of the movable member 170e occurs when movement of the movable element 142e is transferred to the movable member 170e as a result of the magnetic attraction between the two. After the movable element 142e is placed on the protrusion 238 halfway between the "+" or the "−", which corresponds to the initial position of the movable member 170e, the user will move the movable element 142e towards either the "+" or the "−" and the movable member 170e will move with it. Referring to FIG. 27, springs 242 will go into tension and springs 242 go into compression as the movable member 170e moves in the direction of the "+" and the tensioning and compression continues until the movable element reaches the "+." At this point, the spring force will overcome the magnetic force and return the movable member 170e to the initial position. The springs 242 and 244 will also return the movable member 170e to the initial position if the movable element is pulled off the wall 144e. This process, which is identical in the "−" direction, may be repeated until the desired increase or decrease is accomplished.

Figure 28:
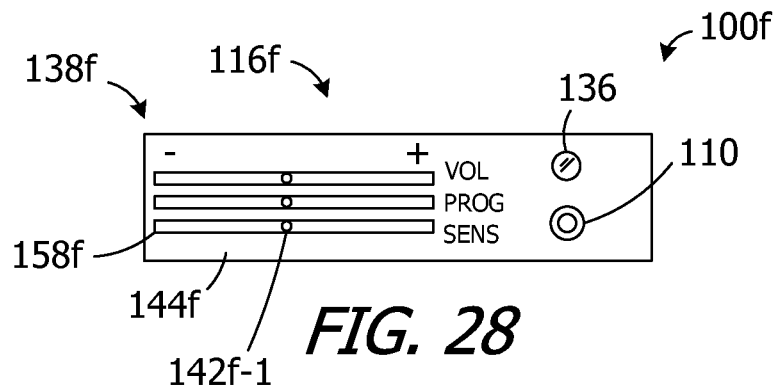
FIG. 28 is a top view of a sound processor, with a control panel, in accordance with one embodiment of a present invention with the rotatable element detached.
Figure 29:
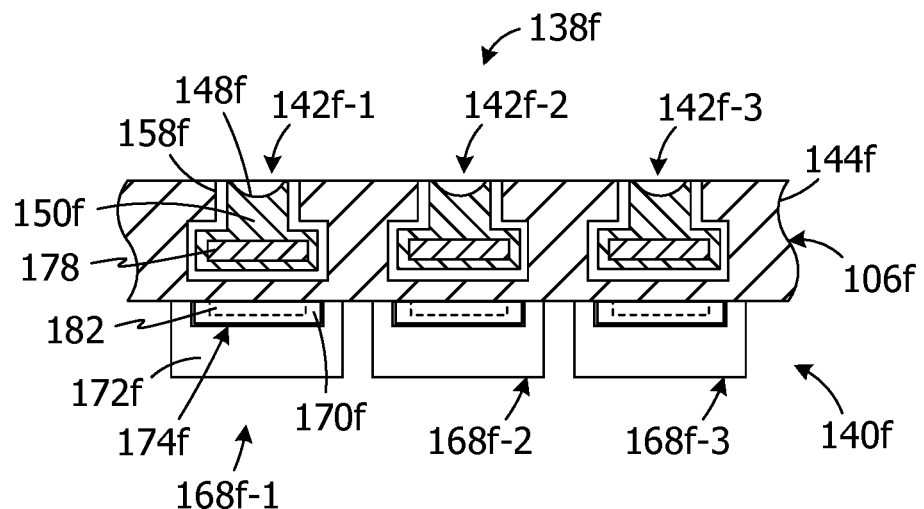
FIG. 29 is a partial section view of the control panel illustrated in FIG. 28.

Another example of a sound processor that includes a control panel which responds to linear movement is generally represented by reference numeral 100f in FIG. 28. The exemplary sound processor 100f illustrated in FIGS. 28 and 29 is substantially identical to sound processor 100e and similar elements are represented by similar reference numerals. For example, the sound processor 100f includes a housing 106f and a control panel 116f with an internal portion 138f that is separated from an internal portion 140f by a wall 144f. The control panel wall 144f does not include an opening that extends completely therethrough. Here, however, the external portion 138f also includes a plurality of linearly movable elements 142f-1, 142f-2 and 142-f3 that are magnetically coupled to a respective plurality of linear movement responsive control devices 168f-1, 168f-2 and 168f-3.

The exemplary movable elements 142f-1, 142f-2 and 142-f3 are configured to slide within T-shaped channels 158f and, to that end, each includes a T-shaped magnet carrier 150f that carries a magnet 178. Although knobs which protrude from the channels 158f may be provided in some implementations, given the relatively small size of the control panel the illustrated magnet carriers 150f each includes an indentation 148f that is configured to receive, for example, the tip of a pen or other similar device. The pen or other similar device may then be used to push the associated movable element in the desired direction.

The linear movement responsive control devices 168f-1, 168f-2 and 168f-3 are similar to that described above with reference to FIGS. 25-27. Each has a portion which is magnetically coupled to, and moves with, the movable element 142f and each is operably connected to the sound processor circuitry 108 (or other control circuitry) and produce a control output in response to the movement of a portion thereof. Although the control devices 168f-1, 168f-2 and 168f-3 may be, for example, linear potentiometers or a series of linearly spaced switches, the illustrated examples are linear encoders. To that end, each of the linear movement responsive control devices 168f-1, 168f-2 and 168f-3 includes a movable member 170f as well as a fixed portion 172f with a channel 174e for the movable member. The movable member 170e carries a magnet 182 which cooperates with the magnets 178 in the manner described above. A plurality of light source and sensor arrangements (not shown) are arranged along the channels 174*f* to detect movement of the movable members 170*f*.

The movable member 170*e* in the illustrated implementation also has an initial position (note FIG. 28) and one or more springs (or other biasing elements) may be provided in the manner described above with reference to FIGS. 26 and 27.

Although the inventions disclosed herein have been described in terms of the preferred embodiments above, numerous modifications and/or additions to the above-described preferred embodiments would be readily apparent to one skilled in the art. By way of example, but not limitation, one or more of the magnets described above may be replaced by magnetic material. Also, the control panels described herein may be part of a control header that is separable from the remainder of the sound processor. The inventions also include any combination of the elements from the various species and embodiments disclosed in the specification that are not already described. It is intended that the scope of the present inventions extend to all such modifications and/or additions and that the scope of the present inventions is limited solely by the claims set forth below.

I claim:

1. A hearing assistance system, comprising:
   a hearing apparatus including a housing, sound processor circuitry within the housing, and an internal control device within the housing, operably connected to the sound processor circuitry, and having a control device rotatable member and a first plurality of magnets, each internal control device rotatable member magnet defining a north/south orientation and at least two of the internal control device rotatable member magnets have different north/south orientations; and
   an external control device, which is not secured to the hearing apparatus, including a second plurality of magnets, each external control device magnet defining a north/south orientation and at least two of the external control device magnets having different north/south orientations; and
   wherein the number of magnets in the first plurality of magnets is different than the number of magnets in the second plurality of magnets; and
   wherein the external control device, when oriented in a predetermined manner relative to the internal control device, is magnetically coupled to the internal control device rotatable member such that rotation of the external control device results in corresponding rotation of the internal control device rotatable member.

2. A hearing assistance system as claimed in claim 1, further comprising:
   an internal lock that substantially prevents rotation of the internal control device rotatable member when in a locked state and does not prevent movement of the internal control device rotatable member when in an unlocked state.

3. A hearing assistance system as claimed in claim 2, wherein
   the internal lock is biased to the locked state and is configured to move to the unlocked state in response to the presence of the external control device.

4. A hearing assistance system as claimed in claim 1, wherein
   the housing includes a wall, located between the external control device and the internal control device rotatable member, that does not include an aperture that extends completely therethrough.

5. A hearing assistance system as claimed in claim 1, wherein
   rotation of the internal control device rotatable member turns the hearing apparatus on and off.

6. A hearing assistance system as claimed in claim 1, wherein
   the sound processor circuitry adjusts an operational parameter selected from the group consisting of volume, sensitivity, and program in response to movement of the control device rotatable member.

7. A hearing assistance system as claimed in claim 1, wherein
   the hearing apparatus housing includes a circular mounting structure; and
   the external control device includes a knob, in which the second plurality of magnets is located, that is configured to fit into the circular mounting structure.

8. A hearing assistance system as claimed in claim 1, wherein
   the internal control device includes an encoder or a potentiometer.

9. A hearing assistance system, comprising:
   a hearing apparatus including a housing, sound processor circuitry within the housing, an internal control portion within the housing that has a rotatable element and is operably connected to the sound processor circuitry, and an internal lock within the housing that substantially prevents movement of the internal control portion when in a locked state and does not prevent movement of the internal control portion when in an unlocked state; and
   an external control portion, which is not secured to the housing, including a magnet that magnetically couples with the internal control portion rotatable element such that rotation of the external control portion results in rotation of the internal control portion rotatable element;
   wherein the internal lock is biased to the locked state and is configured to move to the unlocked state in response to the presence of the external control portion magnet and to return to the locked state in response to the absence of the external control portion magnet; and
   wherein the hearing apparatus adjusts an operational parameter selected from the group consisting of on-off, volume, sensitivity, and program in response to movement of the internal control portion rotatable element.

10. A hearing assistance system as claimed in claim 9, wherein
    the internal control portion includes an encoder or a potentiometer.

11. A hearing assistance system as claimed in claim 9, wherein
    the hearing apparatus housing includes a circular mounting structure; and
    the external control portion includes a knob, in which the magnet is located, that is configured to fit into the circular mounting structure.

12. A hearing assistance system, comprising:
    a hearing apparatus including a housing, sound processor circuitry within the housing, an internal control device, within the housing, operably connected to the sound processor circuitry and including a linearly movable member; and
    an external control device, which is not secured to the hearing apparatus, configured to magnetically couple to the internal control device linearly movable member such that linear movement of the external control device results in linear movement of the internal control device linearly movable member.

13. A hearing assistance system as claimed in claim 12, wherein
the internal control device includes an encoder or a potentiometer.

14. A hearing assistance system as claimed in claim 12, wherein
the hearing apparatus housing includes an exterior with a linear mounting structure; and
the external control device is configured to be removably mounted to the linear mounting structure such that the external control device is linearly movable along the linear mounting structure when mounted to the linear mounting structure.

15. A hearing assistance system as claimed in claim 14, wherein
the linear mounting structure is a recess or a protrusion.

16. A hearing assistance system as claimed in claim 12, wherein
the internal control device includes a first plurality of magnets, each internal control device magnet defining a north/south orientation and at least two of the internal control device magnets having different north/south orientations; and
the external control device includes a second plurality of magnets, each external control device magnet defining a north/south orientation and at least two of the external control device magnets having different north/south orientations; and
the number of magnets in the first plurality of magnets is different than the number of magnets in the second plurality of magnets.

17. A method of controlling a hearing apparatus, comprising the step of:
unlocking a portion of an internal encoder or potentiometer with a magnet of an external control device;
magnetically coupling the magnet of the external control device with the portion of the internal encoder or potentiometer; and
controlling the hearing apparatus by imparting movement to the unlocked portion of the internal encoder or potentiometer with the external control device that is magnetically coupled to the internal encoder or potentiometer.

18. A method as claimed in claim 17, wherein
imparting movement comprises rotating the magnetically coupled external control device to cause the portion of the internal encoder or potentiometer to rotate.

19. A method as claimed in claim 17, wherein
imparting movement comprises linearly moving the magnetically coupled external control device to cause the portion of the internal encoder or potentiometer to move linearly.

20. A method as claimed in claim 17, wherein
controlling the hearing apparatus comprises turning the hearing apparatus on or off.

21. A method as claimed in claim 17, wherein
controlling the hearing apparatus comprises adjusting an operational parameter selected from the group consisting of volume, sensitivity, and program.

* * * * *